(12) United States Patent
Hallack et al.

(10) Patent No.: US 11,175,233 B2
(45) Date of Patent: Nov. 16, 2021

(54) TACTICAL CHEMICAL DETECTOR

(71) Applicants: GENTEX CORPORATION, Zeeland, MI (US); VAPORSENS, Salt Lake City, UT (US)

(72) Inventors: Jason D. Hallack, Allendale, MI (US); Bradley R. Hamlin, Allendale, MI (US); Jeffrey K. Okamitsu, Westminster, MD (US); Ross A. Riches, Sandy, UT (US); Douglas W. Later, Sandy, UT (US); Benjamin R. Bunes, Murray, UT (US)

(73) Assignee: GENTEX CORPORATION, Zeeland, MI (US)

( * ) Notice: Subject to any disclaimer, the term of this patent is extended or adjusted under 35 U.S.C. 154(b) by 0 days.

(21) Appl. No.: 16/801,540

(22) Filed: Feb. 26, 2020

(65) Prior Publication Data

US 2020/0326286 A1    Oct. 15, 2020

Related U.S. Application Data

(60) Provisional application No. 62/811,262, filed on Feb. 27, 2019.

(51) Int. Cl.
*G01N 31/22* (2006.01)
*G08B 7/06* (2006.01)
*G01N 21/75* (2006.01)
*G01N 33/00* (2006.01)

(52) U.S. Cl.
CPC .......... *G01N 21/75* (2013.01); *G01N 31/225* (2013.01); *G01N 33/004* (2013.01);
(Continued)

(58) Field of Classification Search
CPC .... G01N 21/75; G01N 31/225; G01N 33/004; G01N 33/0047; G01N 2201/061;
(Continued)

(56) References Cited

U.S. PATENT DOCUMENTS 6,379,969 B1 * 4/2002 Mauze ............... G01N 21/6428
422/82.05
10,307,090 B2 * 6/2019 Rudmann .......... G01N 21/3504
(Continued)

OTHER PUBLICATIONS

International Search Report, dated May 28, 2020 for corresponding PCT application No. PCT/US2020/019817, 2 pages.
(Continued)

*Primary Examiner* — Isiaka O Akanbi
(74) *Attorney, Agent, or Firm* — Price Heneveld LLP; Brian James Brewer

(57) ABSTRACT

A tactical chemical detector may include a light array comprising a plurality of light sources; a sensor optic comprising a plurality of optic elements, each optic element in optical communication with one of the plurality of light sources; a sensor array comprising a plurality of sensors arranged on a substrate, each sensor in optical communication with one of the plurality of light sources and wherein at least one vent opening extends through the substrate; a power source configured to selectively provide power the light array and the sensor array; and a housing having a first side and a second side and enclosing the light array, the sensor optic, the sensor array, and the power source.

18 Claims, 5 Drawing Sheets

(52) U.S. Cl.
CPC ........... *G01N 33/0047* (2013.01); *G08B 7/06* (2013.01); *G01N 2201/061* (2013.01); *G01N 2201/068* (2013.01)

(58) Field of Classification Search
CPC .. G01N 2201/068; G01N 21/78; G01N 21/59; G01N 21/6454; G01N 21/6428; G01N 21/77; G01N 2021/77869; G01N 2021/7793; G08B 7/06; Y10T 436/144444; Y10T 436/147777
USPC .................................................. 356/432, 343
See application file for complete search history.

(56) References Cited

U.S. PATENT DOCUMENTS

| | | | |
|---|---|---|---|
| 2010/0271220 A1* | 10/2010 | Pattok | G08B 17/103 340/628 |
| 2012/0241623 A1 | 9/2012 | Camy et al. | |
| 2012/0301361 A1 | 11/2012 | Cates | |
| 2015/0097666 A1* | 4/2015 | Boyd | H04L 67/10 340/517 |
| 2017/0316487 A1* | 11/2017 | Mazed | G06Q 30/02 |

OTHER PUBLICATIONS

Written Opinion of the International Searching Authority dated May 28, 2020 for corresponding PCT application No. PCT/US2020/019817, 5 pages.

* cited by examiner

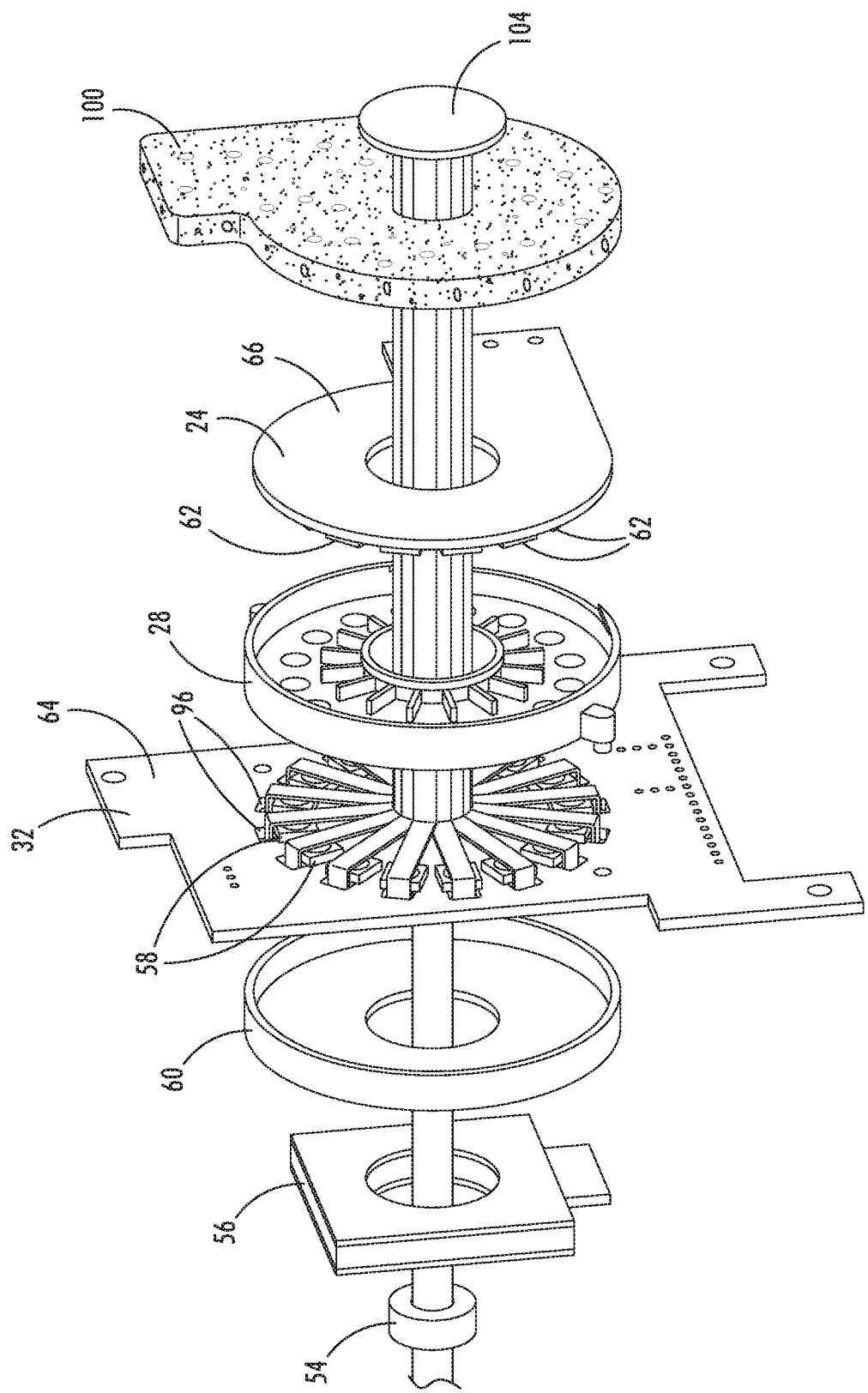

TACTICAL CHEMICAL DETECTOR

CROSS REFERENCE TO RELATED APPLICATIONS

This application claims the benefit of and priority to U.S. Provisional Patent Application No. 62/811,262, filed on Feb. 27, 2019, entitled Tactical Chemical Detector, the entire disclosure of which is hereby incorporated herein by reference.

FIELD OF THE DISCLOSURE

This disclosure relates generally to detectors, and in particular, to detectors for particular chemicals or contaminants.

SUMMARY

In an aspect, a tactical chemical detector may comprise a light array comprising a plurality of light sources; a sensor optic comprising a plurality of optic elements, each optic element in optical communication with one of the plurality of light sources; a sensor array comprising a plurality of sensors arranged on a substrate, each sensor in optical communication with one of the plurality of light sources, at least one vent opening extending through the substrate; a power source configured to selectively provide power to the light array and the sensor array; and a housing having a first side and a second side. The housing may enclose the light array, the sensor optic, and the sensor array. The sensors may comprise nanofiber chemical sensors; and at least a plurality of nanofibers in at least one sensor may have been synthesized with specific functional groups to allow the sensors to interact with particular materials. The tactical chemical detector may further comprise a pump, a first opening in the first side of the housing, and a second opening in the second side of the housing; and the pump may be configured to pump fluid through into the tactical chemical detector through the first opening, across the sensor array, and out of the tactical chemical detector through the second opening. The optic elements may be configured to collimate light from the light sources.

The tactical chemical detector may further comprise a hydrophobic material configured to reduce or eliminate moisture from entering the tactical chemical detector. The first side of housing may define a first opening. The hydrophobic material may be disposed within the housing. The hydrophobic may cover the first opening in the housing. The tactical chemical detector may further comprise a filter covering the first opening. The hydrophobic material may be disposed between the filter and the first wall of housing, covering the first opening. The tactical chemical detector may further comprise at least one additional sensor; wherein the at least one additional sensor is configured to detect at least one of oxygen levels, carbon monoxide levels, ethylene oxide, and lower explosive limits of explosive vapors in the atmosphere.

The sensor optic may be generally annular. The sensor optic may define a generally circular opening therethrough. The first side of the housing may define a first opening and the second side of the housing may define a second opening; and the first opening, the second opening, and the opening defined through the sensor optic may be generally aligned with one another. The first and second openings may be generally circular, and the first opening, the second opening, and the opening defined through the sensor optic may be generally coaxially aligned with one another. The tactical chemical detector may further comprise a haptic motor disposed within the housing and in communication with the sensor array, and operable to create a vibration in the tactical chemical detector. The tactical chemical detector may further comprise a piezoelectric element disposed within the housing and in communication with the sensor array. The piezoelectric element may be configured to generate an audible alert upon the detection of a particular chemical. The tactical chemical detector may further comprise at least one alerting light source disposed within the housing and in communication with the sensor array. The housing may further define at least one secondary opening; and each of the at least one alerting light sources may be disposed adjacent to one of the at least one secondary openings. The tactical chemical detector may further comprise a display panel in the housing, and in communication within the sensor array. The tactical chemical detector may further comprise a clip secured to the housing. The tactical chemical detector may further comprise at least one acknowledgment button disposed on the housing and operable to turn off an alert.

In an aspect, a sensing assembly may comprise a light array comprising a plurality of light sources; a sensor optic comprising a plurality of optic elements, each optic element in optical communication with one of the plurality of light sources; and a sensor array comprising a plurality of sensors disposed on a substrate, each sensor in optical communication with one of the plurality of light sources. At least one vent opening may extend through the substrate of the sensor array. The sensing assembly may further comprise at least one mixing baffle disposed on sensor optic and configured to direct a fluid over at least one of the plurality of sensors. The plurality of sensors may be arranged in proximity to one another on the substrate. The plurality of sensors may be arranged in a circular configuration. A plurality of vent openings may be disposed around an outer perimeter of the sensors. Each of the sensors may be associated with at least one vent opening. The sensor optic may be generally annular in shape. The sensor optic may comprise a collector side configured to accept the light array and an emitter side comprising a plurality of mixing baffles; and a plurality of optic elements may extend through sensor optic between collector side and emitter side. The at least one light source in the light array may comprise light emitting diodes. The sensors may be nanofiber-based chemical sensors. The optic elements may be configured to collimate light from the light sources.

In an aspect, a sensor optic having a collector side and an emitter side may comprise at least one mixing baffle disposed on the emitter side; and a plurality of optic elements may extend through sensor optic from collector side to emitter side. The collector side of the sensor optic may be configured to accept a light array comprising at least one light source; and each optic element may be in optical communication with a light source. The sensor optic may be generally annular in shape and may define an opening extending therethrough. The optic elements may be disposed around the opening. The at least one mixing baffle may extend generally from a position proximate the opening toward an outer perimeter of the sensor optic. The optic elements may be configured to collimate light from light sources.

In an aspect, a method for detecting chemicals or contaminants comprises: providing a tactical chemical detector having a light source configured to provide light to a plurality of sensors; collimating the light source; directing the collimated light to the plurality of sensors; pumping a fluid through the tactical chemical detector; and causing the fluid to pass over the plurality of sensors disposed within the tactical chemical detector. The fluid may be air. The sensors may comprise nanofiber chemical sensors. A sensing assembly of the tactical chemical detector may comprise a plurality of mixing baffles configured to direct the fluid toward each of the nanofiber chemical sensors. The method may further comprise the step of directing the fluid through one of a plurality of vent openings after the fluid has passed over the sensors. The method may further comprise the steps of: providing at least one of a haptic motor, a piezoelectric element, and an alert light source and associated printed circuit board; and causing at least one of the haptic motor, the piezoelectric element, and the alert light source and associated printed circuit board to generate an alert upon the detection, by the nanofiber chemical sensors, of a particular chemical.

BRIEF DESCRIPTION OF THE DRAWINGS

FIG. 5 illustrates air flow through the device of FIG. 1; and

DETAILED DESCRIPTION

In some circumstances, it may be advantageous to detect specific chemicals or contaminants in the environment, and in particular, airborne contaminants. Airborne contaminants may include toxic industrial chemicals (TICs), chemical warfare agents (CWAs), and non-traditional agents (NTAs). These contaminants can attack skin, blood, the respiratory system, and nervous system, leading to illness, incapacitation, and, with a sufficiently high dose, death. Explosive vapors represent another threat. For example, air enriched with fuel at an appropriate ratio can be ignited by firing a weapon. Confined space threats may include oxygen levels, carbon monoxide, hydrogen sulfide, and the like. Low levels of oxygen can cause asphyxiation while high levels can cause hyperoxia that causes disorientation, seizures, and nervous system damage. In some embodiments, the presence of these conditions may result in proximate danger to exposed personnel, and may indicate an imminent or ongoing threat. In some circumstances, the presence of certain chemicals may indicate a leak or a failure in storage or processing of the chemical. A handheld or wearable chemical detector may be used to detect a specific chemical or chemicals in the environment of the detector and may be configured to transmit or display information about the presence of the specific chemical or chemicals. This may provide those exposed to the chemicals an opportunity to take appropriate steps to minimize risks by carrying out measures to protect themselves, such as donning personal protective equipment (PPE).

Figure 1:
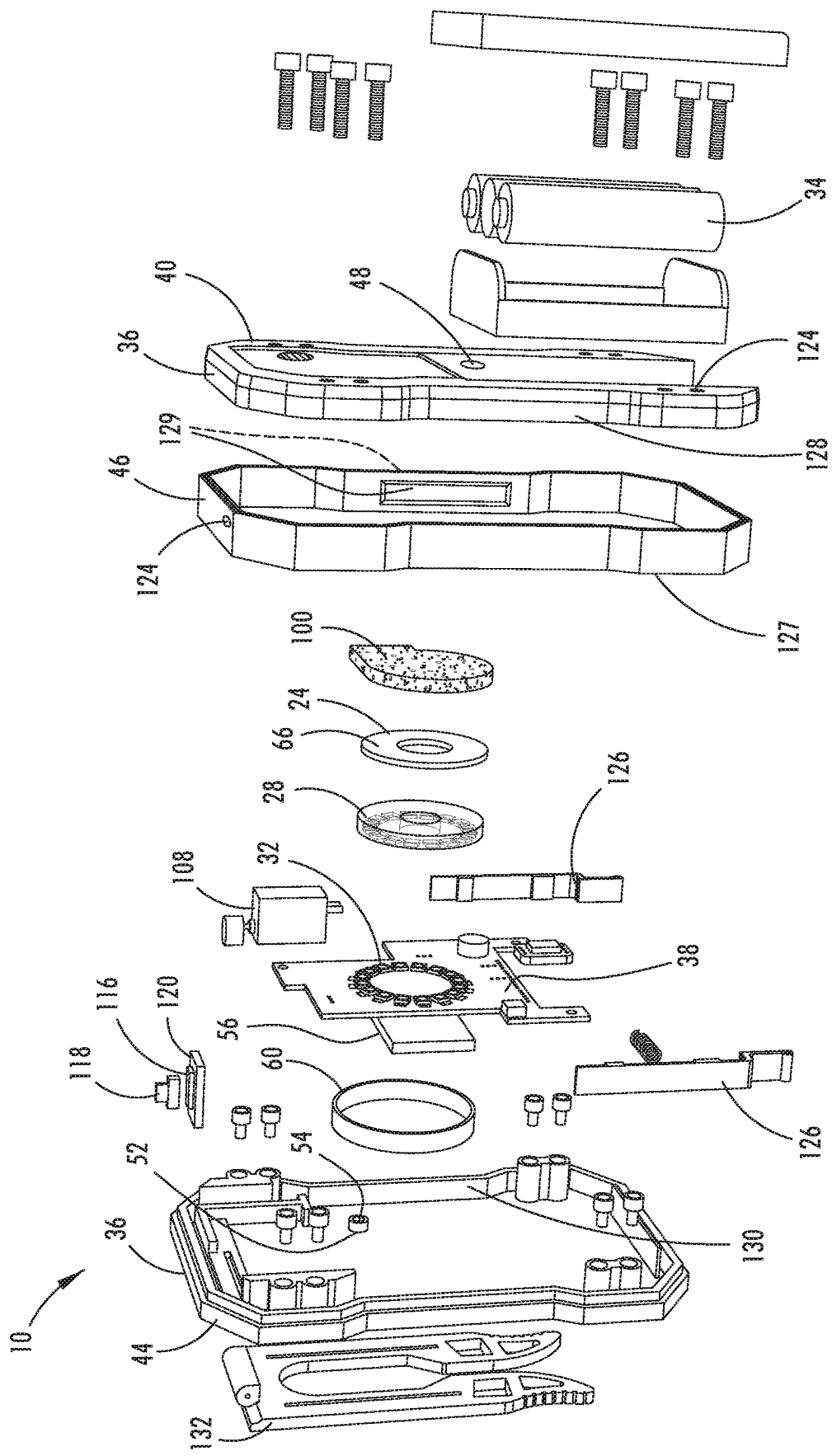
FIG. 1 illustrates an exploded view of a tactical chemical detector in accordance with this disclosure.
Figure 2:
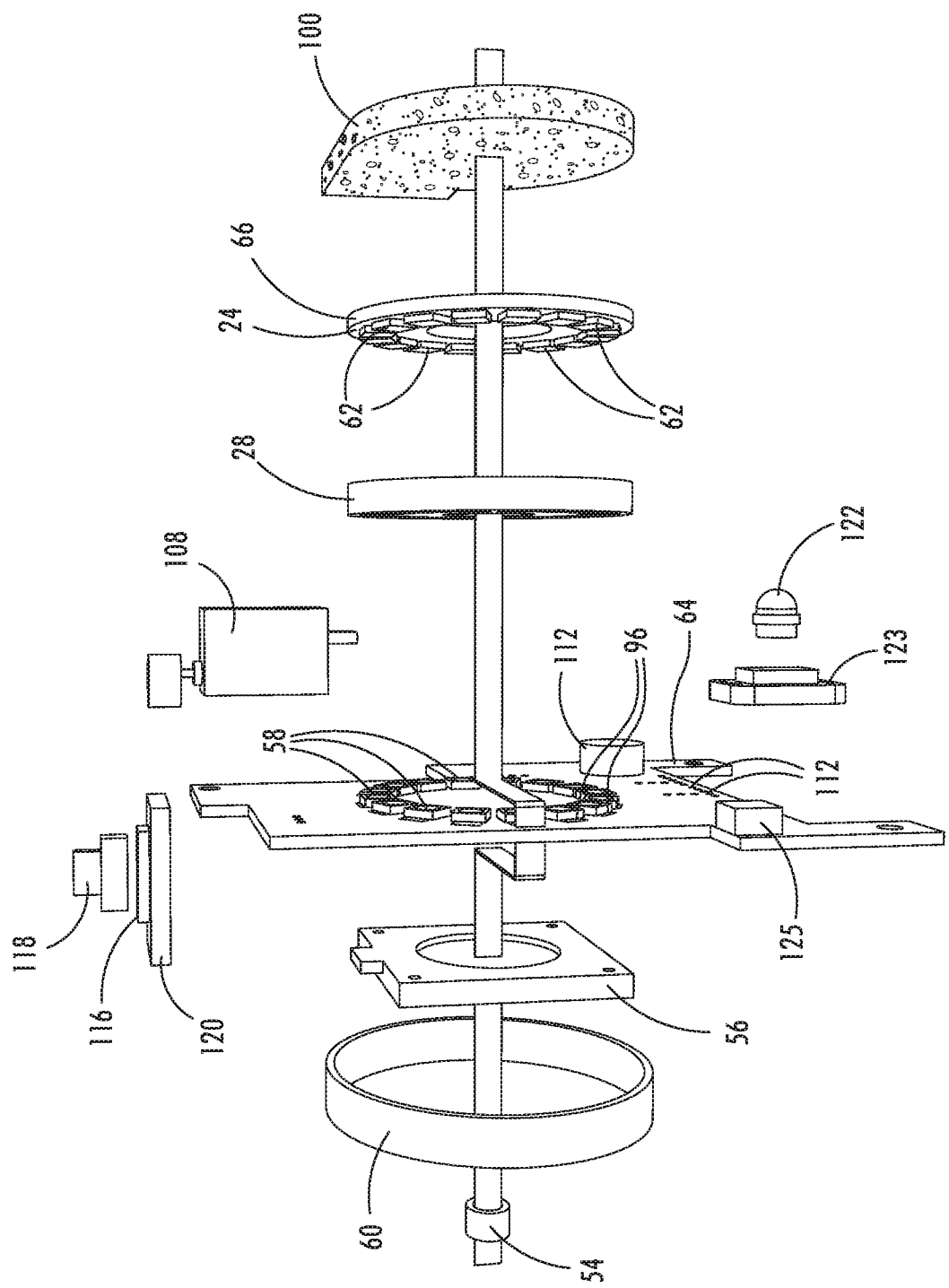
FIG. 2 illustrates an exploded view of a portion of the tactical airborne chemical detector of FIG. 1, and includes some of the components directed to the sensing capabilities of the device and that control airflow through the device.
Figure 3:
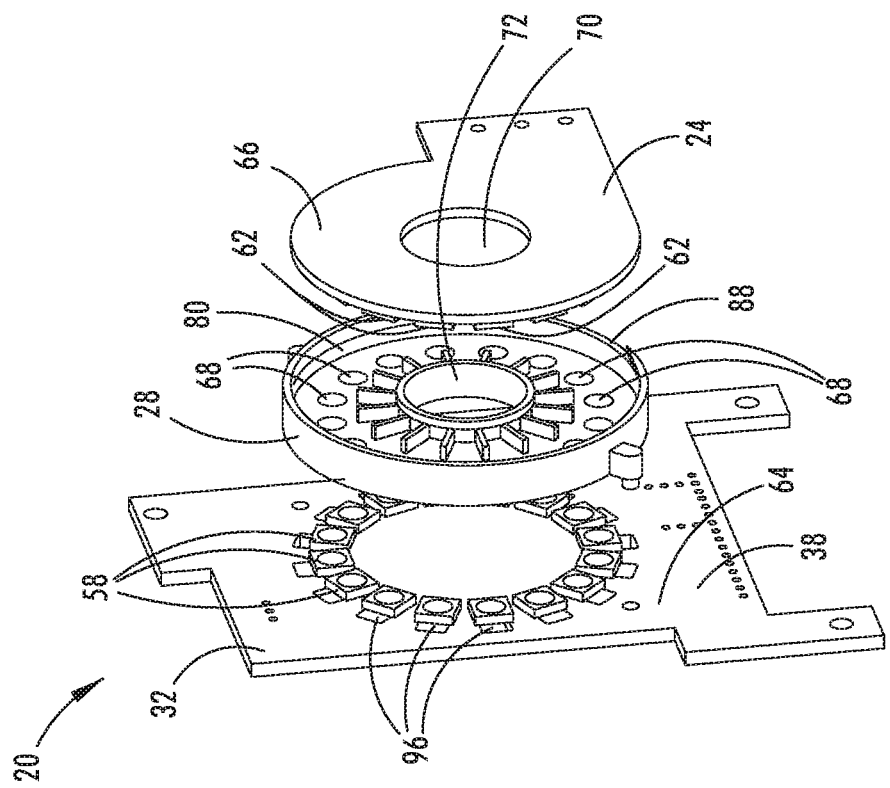
FIG. 3 illustrates a sensing assembly of an airborne chemical detector in accordance with this disclosure.

Referring to FIGS. 1-3, a tactical chemical detector, shown generally at 10, may comprise a sensing assembly 20 comprising a light array 24; a sensor optic 28; and a sensor array 32. Tactical chemical detector 10 may further comprise a power source 34 configured to selectively provide power to various components of tactical chemical detector 10, including light array 24 and sensor array 32. Sensing assembly 20 may be disposed within a housing 36. Power source 34 may also be disposed within housing 36 of tactical chemical detector 10.

Sensing assembly 20 may be configured to identify particular chemicals or contaminants. The chemicals or contaminants may be airborne chemicals or contaminants. In some embodiments, when a particular chemical or contaminant has been identified by sensing assembly 20, tactical chemical detector 10 may be configured to generate an alert in response to the presence of the chemical or contaminant. Tactical chemical detector 10 may further be configured to display or transmit an indication of the alert.

In some embodiments, sensor array 32 may comprise a substrate 64, and substrate 64 of sensor array 32 may comprise a printed circuit board 38. Printed circuit board 38 may further comprise a control circuit 38. Control circuit 38 may be in communication with sensing assembly 20 and with sensors 58. Control circuit 38 may be configured to receive inputs from sensors and to determine whether particular chemicals or contaminants have been identified.

In some embodiments, sensor array may be configured to be removeable and replaceable by a user.

Housing 36 may have a first side 40 and a second side 44. In some embodiments, housing may further comprise a ring 46, such as an elastomeric ring, extending between and connecting together first side 40 and second side 44 of housing 36. First side 40 of housing 36 may define a first opening 48, and second side 44 of housing 36 may define a second opening 52. Second opening 52 may comprise a vent 54. Vent 54 may be configured to allow air to be released from interior of housing 36 of tactical chemical detector 10.

In some embodiments, tactical chemical detector 10 may further comprise a pump 56. Pump 56 may be disposed in proximity to and in communication with second opening 52 of housing 36. As shown in FIG. 2, pump 56 may be configured to pull air in to tactical chemical detector 10 through first opening 48 in housing 36 and to cause air to pass through sensing assembly 20 and to exit from housing 36 through second opening 52 of housing 36. A rear baffle 60 may be configured to partially enclose pump 56, thereby directing air through second opening 52 rather than allowing air to escape and remain within housing 36 of tactical chemical detector 10. Pump 56 may comprise a blower.

Sensing assembly 20 may be configured to sense particular chemicals or contaminants. Sensor array 32 may comprise a plurality of sensors 58 arranged on a substrate 64, as shown in FIG. 3. Sensors 58 may comprise organic conductive or semiconductive nanofiber chemical sensors. The nanofibers used in sensors 58 may be synthesized with specific functional groups that can interact with airborne chemicals, materials, vapors, and particles. The nanofibers may be deposited on an interdigitated electrode to form an electrode-nanofiber array (hereinafter referred to as a "sensor"). Interaction of the nanofibers with certain materials may change the electrical characteristics of sensor 58. An increase or decrease in a particular electrical characteristic, including measured current or effective resistance, of sensor 58 may occur as a result of these airborne material interactions.

Nanofiber sensors 58 may have excellent sensitivity and selectivity, and may be suitable for miniaturized, low-power devices. Nanofiber sensors 58 may have a small area. For example, in some embodiments, each sensor may be 3 mm×3 mm. This may allow for a high density of sensors 58 in a small instrument. Nanofibers tend to be selective to a class of compounds (e.g., amines). Sensing assembly 20 may be configured to identify specific chemicals based on the aggregate response of the sensor array 32. Detectable chemicals may each produce a unique response signature that can be matched to known and/or predetermined response signatures in a library of response signatures.

Nanofiber sensors 58 may be based on organic nanofibers. The nanofibers may be self-assembled from building block molecules functionalized to interact specifically with certain chemicals or classes of chemicals. Once assembled, the nanofibers may be deposited onto an electrode pair to create chemiresistive sensors (i.e., sensors that signal detection of a chemical by changing electrical resistance). The change in resistance is due to a change in charge carrier density caused by electron transfer with the chemical. The interaction is non-covalent and reversible.

Organic conductive or semiconductive nanofibers with different functional groups may have a different response to the same airborne material. By using one or more different sensors 58 in an array of such sensors, a response signature can be established for a particular airborne material. Sensors 58 can be configured to detect a variety of airborne chemicals, including toxins, combustion by-products, and explosives. Non-limiting examples of suitable nanofibers can be formed by self-assembly of building block compounds such as carbazole-cornered, arylene-ethynylene tetracyclic macromolecules, indolocarbazole derivatives thereof, substituted perylene tetracarboxylic diimide molecule, substituted a 3,4,9,10-tetracarboxyl perylene molecule, and mixtures thereof.

In some embodiments, to activate sensor materials, sensors 58 may be exposed to light. For example, sensor optic 28 may be configured to generally direct light toward sensors 58 in a sufficient magnitude to activate corresponding nanofiber materials. Light may comprise light in the visible spectrum. Light array 24 may be configured to provide light to each of the plurality of sensors 58. Light array 24 may comprise a plurality of light sources 62 disposed on a substrate 66. Substrate 66 may comprise a printed circuit board 38. In some embodiments, light sources 62 may be light emitting diodes. Light sources 62 may be configured to provide light of at least about 8000 lux.

In some embodiments, light array 24 may be generally annular in shape. Light array 24 may define an opening 70 through the center of light array 24. Light sources 62 may be distributed around opening 70. In some embodiments, first and second openings 48, 52 may be generally circular and opening 70 of light array 24 may be coaxially aligned with both first opening 48 in first side 40 of housing 36 and second opening 52 in second side 44 of housing 36.

Sensor optic 28 may be generally annular, and may define a generally circular opening in the center 72 of sensor optic 28. Generally circular opening 72 of sensor optic 28 may be configured to be coaxially aligned with at least one of opening 70 in light array 24, first opening 48 in first side 40 of housing 36 and second opening 52 in second side 44 of housing 36.

Sensor optic 28 may be configured to collimate light and to direct it to the plurality of sensors 58. Sensor optic 28 may have a collector side 80 and an emitter side 84. Sensor optic 28 may comprise a plurality of optic elements 68 extending through sensor optic 28 from collector side 80 to emitter side 84. Each optic element 68 may be in optical communication with one of the plurality of light sources 62. Each optic element 68 may be configured to collect the light from light sources 62 of light array 24 on collector side 80 of sensor array and to emit the light from optic element 68 at emitter side 84 of sensor optic 28. In some embodiments, optic elements 68 may be disposed around a circumference of generally circular opening 72 of sensor optic 28.

In some embodiments, tactical chemical detector may further comprise an array of nanofiber-based sensors combined with at least one additional sensor for ethylene oxide, carbon monoxide, oxygen, and lower explosive limit of explosive vapors (not shown). Nanofiber sensors 58 may not be able to accurately detect ethylene oxide, carbon monoxide, oxygen, and lower explosive limit. A processor (not shown) may be disposed on a printed circuit board (PCB) 120 configured to operate the at least one additional sensor. in some embodiments, the processor may be configured to operate the at least one additional sensor and sensors 58. the processor may also be configured to operate any alerts and algorithms associated with determining the identity of chemicals present.

Figure 4A:
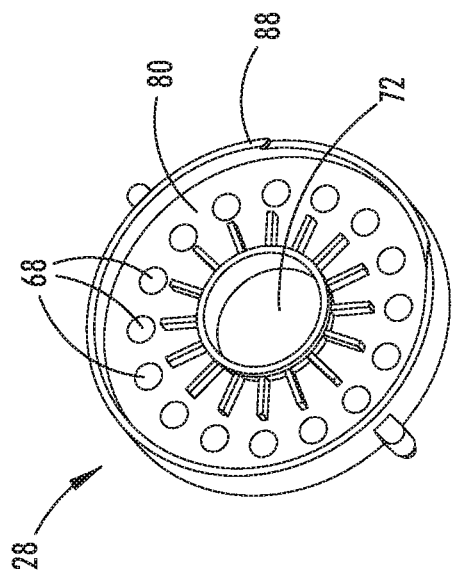
FIG. 4A illustrates a first side of a sensor optic of an airborne chemical detector in accordance with this disclosure.

A lip 88 may extend around an outer perimeter of sensor optic 28, as shown in FIG. 4A. Lip may be configured to allow sensor optic 28 to accept light array 24, thereby securing light array 24 in a position relative to sensor optic 28. Each light source 62 from light array 24 may be associated with an optic element 68. Lip 88 also may also prevent air flowing through center of light array 24 and sensor optic 28 from travelling between sensor optic 28 and light array 24, instead helping to direct air through sensor optic 28 to sensor array 32.

Figure 4B:
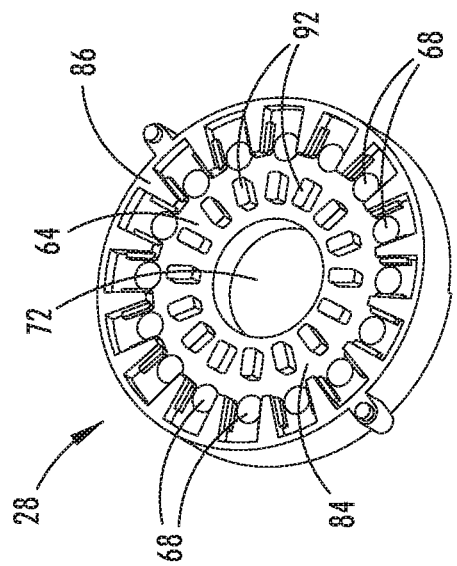
FIG. 4B illustrates a second side of the sensor optic of an airborne chemical detector in accordance with this disclosure.

Emitter side 84 of sensor optic 28 may comprise at least one mixing baffle 92 as shown in FIG. 4B. The at least one mixing baffle 92 may be configured to divert air travelling through center of sensor optic 28, and to distribute the air to travel across the plurality of sensors 58. A wall 86 may extend from a perimeter of emitter side 84 of sensor optic 28 and generally orthogonal to emitter side 84, thereby enabling sensor optic 28 to surround the plurality of sensors 58 on sensor array substrate 64.

In some embodiments, sensor optic 28 may comprise of an optics-grade plastic such as an optics-grade polycarbonate or an optics-grade acrylic. The plurality of optic elements 68 may be integrally formed within sensor optic 28.

Sensor array 32 may comprise a plurality of sensors 58 disposed on substrate 64. Each sensor 58 may be associated with one of the plurality of optic elements 68, and may be in optical communication with at least one light source 62. The plurality of sensors 58 may be disposed in an arrangement on substrate 64 such as, for example, in a circular arrangement. A plurality of vent openings 96 may be disposed around an outer perimeter of the sensor arrangement. In some embodiments, there may be one vent opening 96 associated with each sensor 58. In some embodiments, at least a portion of a vent opening 96 may be disposed between each sensor 58 and wall 86 of sensor optic 28. Wall 86 may direct air flowing between sensor optic 28 and sensor array 32 to exit through the plurality of vent openings 96.

In some embodiments, an air-permeable hydrophobic material 104 may be disposed within housing 36 and may be configured to cover first opening 48 in housing 36. Hydrophobic material 104 may be configured to reduce or prevent moisture from entering housing 36. A filter 100 may be disposed within housing in proximity to first opening 48 such that hydrophobic material may be disposed between filter 100 and first opening 48 of housing 36. Filter 100 may be configured to cover first opening 48 of housing 36, thereby filtering fluids entering housing 36 through first opening 48. Openings in filter 100 may be sized to allow air to pass through into tactical chemical detector 10 but to prevent particles that might foul sensors 58 from passing through.

As shown in FIG. 5, when pump 56 is operating, air may enter tactical chemical detector 10 through first opening 48 in first side 40 of housing 36, flowing first through hydrophobic material 104, then through filter 100. Air may then flow through opening 70 in center of light array 24 and through opening 72 in center of sensor optic 28. Upon reaching substrate 64 of sensor array 32, air may change directions, flowing radially outward between sensor optic 28 and sensor array 32 past the plurality of sensors 58 and toward an outer perimeter of sensor arrangement. The at least one mixing baffle 92 may help to direct air toward each of the plurality of sensors 58. Air may travel across sensors 58 to vent openings 96 disposed in substrate 64 of sensor array 32 along the outer perimeter of sensor arrangement. After passing through substrate 64, air may be confined by rear baffle 60, then drawn by pump 56 through vent 54 in second opening 52 of housing 36 to exit tactical chemical detector 10.

In some embodiments, tactical chemical detector 10 may be configured to produce a haptic alert upon the detection of a particular chemical or chemicals. For example, in some embodiments, tactical chemical detector 10 may further comprise a haptic motor 108. Haptic motor 108 may be in communication with control circuit 38 and, therefore, in communication with sensing assembly 20. Upon a determination by control circuit 38 that a particular chemical has been detected, control circuit 38 may send inputs to cause haptic motor 108 to activate. The determination that a particular chemical has been detected may be based on changes in the electrical characteristics of sensor 58. Upon activation, haptic motor may begin vibrating and may cause tactical chemical detector 10 to vibrate.

In some embodiments, tactical chemical detector 10 may be configured to produce an audible alert upon the detection of a particular chemical or chemicals. For example, in some embodiments, tactical chemical detector 10 may further comprise a piezoelectric element 112. Piezoelectric element 112 may be in communication with control circuit 38 and, therefore, in communication with sensing assembly 20. Upon a determination by control circuit 38 that a particular chemical has been detected, control circuit 38 may send inputs to cause the activation of piezoelectric element 112. The activation of piezoelectric element 112 may cause tactical chemical detector 10 to produce an audible alert.

In some embodiments, tactical chemical detector 10 may be configured to produce a visual alert upon the detection of a particular chemical or chemicals. For example, tactical chemical detector 10 may further comprise at least one light source 116 and an associated printed circuit board (PCB) 120 configured to provide a visual alert. The at least one light source 116 and associated PCB 120 may be in communication control circuit 38 and, therefore, in communication with sensing assembly 20. Housing 36 may comprise at least one light alert opening 124. A transparent or translucent protective shroud (not shown) may cover light alert opening 124. Each light source 116 may be disposed within housing 36 and positioned so that, when light source 116 has been activated, light may shine through light alert opening 124. A light guide 118 may be configured to direct light from light source 116 to light alert opening 124. Each of the at least one light sources 116 and associated PCBs 120 may be in communication with control circuit 38. Upon a determination by control circuit 38 that a particular chemical has been detected, control circuit 38 may send inputs to the at least one light source 116 and associated PCBs 120 that may cause the activation of the at least one light sources 116, thereby producing a visual alert. PCB may also be configured to identify detected chemicals and cause the generation of an alert to notify the user of the presence of a potential threat.

In some embodiments, tactical chemical detector 10 may further comprise a display panel (not shown). Display panel may be in communication with control circuit 38 and, therefore, in communication with sensing assembly 20. Display panel may be configured to display a visual alert upon the detection of a particular chemical.

In some embodiments, alert may remain active until it has been acknowledged. At least one acknowledgement button 126 may be disposed on housing 36. Activating acknowledgement button 126 may activate an activation switch 125 within housing 36 that may terminate alert.

In some embodiments, tactical chemical detector 10 may comprise two acknowledgement buttons 126. For example, a first acknowledgement button 126 may be disposed on a first side 127 of ring 46 or on a first portion 128 of housing. A second acknowledgement button 126 may be disposed on a second side 129 of ring 46 or on a second portion 130 of housing 36. Either of the two acknowledgement buttons 126 may be used to turn off or deactivate alert. Having acknowledgement buttons 126 disposed in two different locations of housing may facilitate acknowledging alerts for both right- and left-handed people since either acknowledgement button 126 may be activated with either hand of a user.

In some embodiments, tactical chemical detector 10 may be configured to produce at least two types of alerts. For example, tactical chemical detector 10 may be configured to produce both an audible and a visual alert. In some embodiments, tactical chemical detector 10 may comprise haptic motor 108, piezoelectric element 112, and an alert light source 122 and an associated PCB 123, and may be configured to produce a haptic alert, an audible alert, and a visual alert. In some embodiments, the alerts may be produced sequentially. For example, if an alert has not been acknowledged within a predetermined amount of time, a second alert may be activated. If the second alert is not acknowledged within a predetermined amount a third alert may be activated. For example, when a particular chemical has been detected, tactical chemical detector 10 may produce a haptic alert. If the haptic alert is not acknowledged within a first predetermined amount of time, tactical chemical detector 10 may then produce an audible alert. If the audible alert is not acknowledged within a second predetermined amount of time, tactical chemical detector 10 may produce a visual alert. In some embodiments, if the alert is still not acknowledged, alerts may be combined or may alternate. For example, tactical chemical detector 10 may alternate a haptic alert with an audible alert, or may combine a haptic alert with an audible alert.

If an alert has sounded and not yet been acknowledged, and tactical chemical detector 10 detects a second chemical, in some embodiments, tactical chemical detector 10 may begin a second alert. For example, if tactical chemical detector 10 has detected a first particular chemical and produced a haptic alert and progressed to an audible alert, and then a second particular chemical is detected, tactical chemical detector 10 may revert to the haptic alert and begin the alert sequence all over.

In some embodiments, tactical chemical detector 10 may comprise a clip 132. Clip 132 may be fastened to or be an integral part of housing 36. Clip 132 may be configured to be able to be securely fastened to a strap, a belt, a pocket or other article of clothing, or other suitable location. Clip 132 may be configured to lock in place, thereby preventing tactical chemical detector 10 from falling off. Clip 132 may be secured to second side of housing 36.

In some embodiments, tactical chemical detector 10 may be configured to self-test. Self-testing may be conducted either based on an input received through a user interface or at a predetermined time interval or at the occurrence of a predetermined event such as tactical chemical detector 10 being turned on. In some embodiments, as part of the self-test function, tactical chemical detector 10 may be configured to indicate whether filter 100, sensor 58, or a battery (not shown) needs to be replaced, and whether the system is operating normally.

Figure 6:
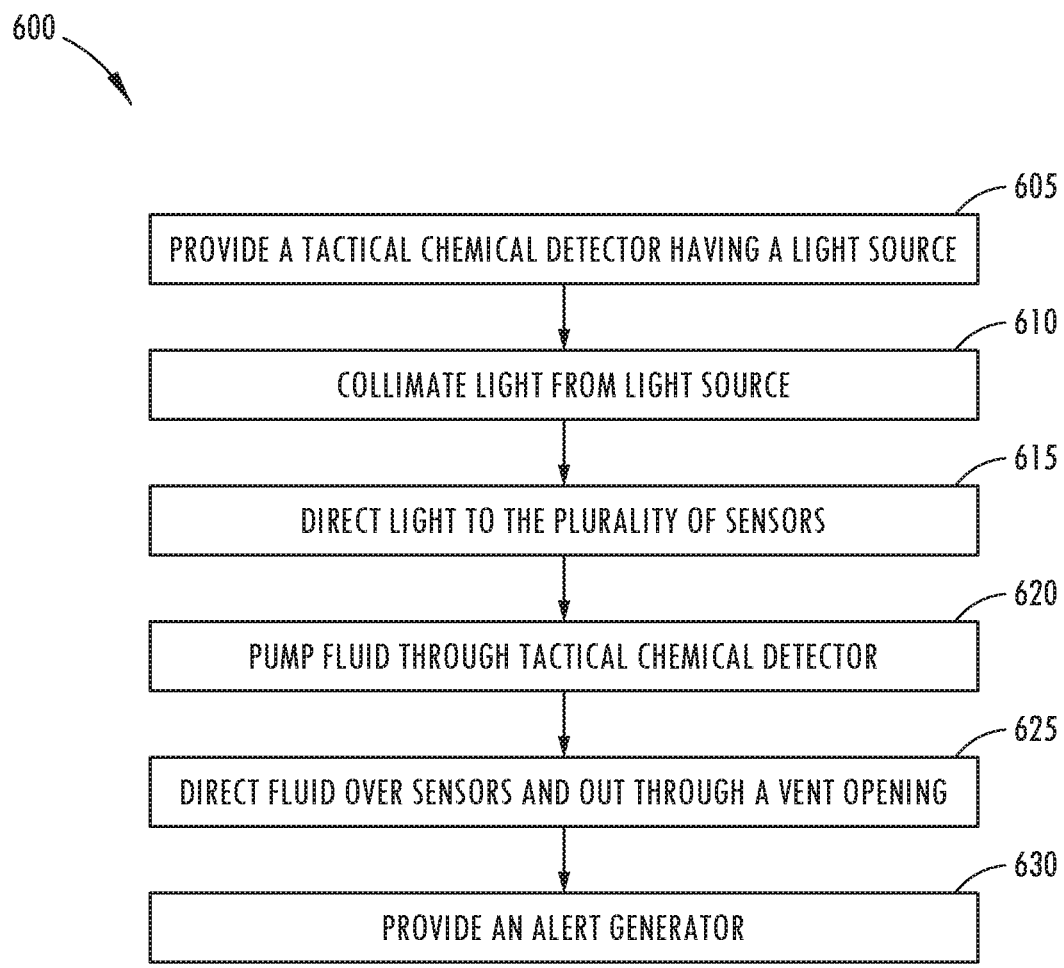
FIG. 6 is a flow chart illustrating a method of detecting chemical contaminants.

Referring to FIG. 6, in some embodiments, a method 600 for detecting chemicals or contaminants may comprise providing a tactical chemical detector 10 having a light source 62 configured to provide light to a plurality of sensors 58 as shown in step 605. Light source 62 may be collimated in step 610. In step 615, the collimated light may be directed to the plurality of sensors 58. In step 620, a fluid may be pumped through the tactical chemical detector. Tactical chemical detector 10 may be configured to cause the fluid to pass over the plurality of sensors 58 disposed within tactical chemical detector 10. The fluid may be air. Sensors 58 may comprise nanofiber chemical sensors. A sensing assembly of tactical chemical detector 10 may comprise a plurality of mixing baffles 92 configured to direct the fluid toward each of the nanofiber chemical sensors 58. In step 625, the fluid may be directed through one of a plurality of vent openings 96 after the fluid has passed over the sensors 58. The method may further comprise the step 630 of providing at least one of a haptic motor 108, a piezoelectric element 112, and an alert light source 122 and associated printed circuit board 123; and causing at least one of the haptic motor 108, the piezoelectric element 112, and the alert light source 122 and associated printed circuit board 123 to generate an alert upon the detection, by the nanofiber chemical sensors, of a particular chemical.

The above description is considered that of the preferred embodiments only. Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims as interpreted according to the principles of patent law, including the doctrine of equivalents.

It should be noted that references to "front," "back," "rear," "upward," "downward," "inner," "outer," "right," and "left" in this description are merely used to identify the various elements as they are oriented in the FIGURES. These terms are not meant to limit the element which they describe, as the various elements may be oriented differently in various applications.

The invention claimed is:

1. A tactical chemical detector comprising:
a light array comprising a plurality of light sources;
a sensor optic comprising a plurality of optic elements, each optic element in optical communication with one of the plurality of light sources;
a sensor array comprising a plurality of sensors comprising nanofiber chemical sensors, the sensors arranged on a substrate, each sensor in optical communication with one of the plurality of light sources;
a power source configured to selectively provide power to the light array and the sensor array; and
a housing having a first side and a second side;
wherein at least a plurality of nanofibers in at least one sensor have been synthesized with specific functional groups to allow the sensors to interact with particular materials;
wherein the housing encloses the light array, the sensor optic, and the sensor array; and
wherein at least one vent opening extends through the substrate.

2. The tactical chemical detector of claim 1, further comprising a pump, a first opening in the first side of the housing, and a second opening in the second side of the housing;
wherein the pump is configured to pump fluid through into the tactical chemical detector through the first opening, across the sensor array, and out of the tactical chemical detector through the second opening.

3. The tactical chemical detector of claim 1, further comprising a hydrophobic material configured to reduce or eliminate the amount of moisture entering the tactical chemical detector;
wherein the first side of housing defines a first opening; and
wherein the hydrophobic material at least partially covers the first opening in the housing.

4. The tactical chemical detector of claim 3, further comprising a filter disposed within the one or more housing;
wherein the filter at least partially covers the first opening.

5. The tactical chemical detector of claim 1, wherein the sensor optic is generally annular;
wherein the sensor optic defines a generally circular opening therethrough;
wherein the first side of the housing defines a first opening;
wherein the second side of the housing defines a second opening; and
wherein the first opening, the second opening, and the opening defined through the sensor optic are generally aligned with one another.

6. The tactical chemical detector of claim 1, further comprising at least one of a haptic motor, a piezoelectric element, an alerting light source, and a display panel disposed within the housing and in communication with the sensor array, each operable to generate an alert in the tactical chemical detector.

7. The tactical chemical detector of claim 6, further comprising at least one additional sensor; wherein the at least one additional sensor is configured to detect at least one of oxygen levels, carbon monoxide levels, ethylene oxide, and lower explosive limits of explosive vapors.

8. The tactical chemical detector of claim 1, wherein the plurality of optic elements are configured to generally collimate light from the light sources; and wherein each of the plurality of sensors is in optical communication with one of the plurality of light sources via at least one of the plurality of optic elements.

9. A sensing assembly comprising:
a light array comprising a plurality of light sources;
a sensor optic comprising a plurality of optic elements, each optic element in optical communication with one of the plurality of light sources; and
a sensor array comprising a plurality of sensors disposed on a substrate, each sensor comprising nanofiber chemical sensors, and each sensor in optical communication with one of the plurality of light sources;
wherein at least a plurality of nanofibers in at least one sensor have been synthesized with specific functional groups to allow the sensors to interact with particular materials; and
wherein at least one vent opening extends through the substrate of the sensor array.

10. The sensing assembly of claim 9, further comprising at least one mixing baffle disposed on the sensor optic and configured to direct a fluid over at least one of the plurality of sensors.

11. The sensing assembly of claim 9, wherein the plurality of sensors are arranged in proximity to one another on the substrate in a generally circular arrangement; and
wherein a plurality of vent openings are disposed around an outer perimeter of the sensors.

12. The sensing assembly of claim 11, wherein each of the sensors is associated with at least one vent opening.

13. The sensing assembly of claim 9, wherein the sensor optic is generally annular in shape;
wherein the sensor optic comprises a collector side configured to accept the light array and an emitter side comprising a plurality of mixing baffles; and
wherein a plurality of optic elements extends through sensor optic between collector side and emitter side.

14. The sensing assembly of claim 9, wherein the optic elements are configured to generally collimate light from the light sources; and
wherein each of the plurality of sensors is in optical communication with one of the plurality of light sources via at least one of the plurality of optic elements.

15. A sensor optic having a collector side and an emitter side, the sensor optic comprising:
at least one mixing baffle disposed on the emitter side; and
a plurality of optic elements extending through sensor optic from collector side to emitter side, each optic element associated with a sensor comprising nanofiber chemical sensors;
wherein at least a plurality of nanofibers in at least one sensor have been synthesized with specific functional groups to allow the sensors to interact with particular materials;
wherein the sensor optic may be generally annular in shape;
wherein sensor optic defines an opening extending therethrough;
wherein the sensor optic is capable of collimating light and directing it to a plurality of sensors; and
wherein the optic elements are disposed around the opening.

16. The sensor optic of claim 15, wherein the collector side of the sensor optic is configured to accept a light array comprising at least one light source; and
wherein each optic element is in optical communication with a light source.

17. The sensor optic of claim 15, wherein the at least one mixing baffle extends generally from a position proximate the opening toward an outer perimeter of the sensor optic.

18. The sensor optic of claim 15, wherein the plurality of optic elements are configured to generally collimate light from light sources.

* * * * *